(12) United States Patent
Mizushima et al.

(10) Patent No.: US 8,921,527 B2
(45) Date of Patent: Dec. 30, 2014

(54) ANTIBODY-CONTAINING SOLUTION FORMULATIONS

(75) Inventors: Hidefumi Mizushima, Tokyo (JP); Eiichi Miyauchi, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 532 days.

(21) Appl. No.: 12/184,551

(22) Filed: Aug. 1, 2008

(65) Prior Publication Data
US 2008/0306247 A1  Dec. 11, 2008

Related U.S. Application Data

(62) Division of application No. 10/504,025, filed as application No. PCT/JP03/01562 on Feb. 14, 2003.

(30) Foreign Application Priority Data

Feb. 14, 2002  (JP) .................................. 2002-36244

(51) Int. Cl.
| | | |
|---|---|---|
| C07K 16/18 | (2006.01) | |
| C07K 16/30 | (2006.01) | |
| C07K 16/44 | (2006.01) | |
| A61K 47/12 | (2006.01) | |
| A61K 47/26 | (2006.01) | |
| A61K 9/00 | (2006.01) | |
| A61K 47/10 | (2006.01) | |
| C07K 16/40 | (2006.01) | |
| C07K 16/42 | (2006.01) | |
| A61K 39/395 | (2006.01) | |
| A61K 39/00 | (2006.01) | |

(52) U.S. Cl.
CPC .............. *C07K 16/44* (2013.01); *C07K 16/3061* (2013.01); *A61K 2039/505* (2013.01); *A61K 47/12* (2013.01); *A61K 47/26* (2013.01); *A61K 39/39591* (2013.01); *A61K 9/0019* (2013.01); *A61K 47/10* (2013.01); *C07K 16/40* (2013.01)
USPC .................... 530/388.1; 530/387.1; 424/130.1

(58) Field of Classification Search
None
See application file for complete search history.

(56) References Cited

U.S. PATENT DOCUMENTS

| | | | |
|---|---|---|---|
| 6,187,304 B1 * | 2/2001 | Jin et al. ..................... | 424/85.5 |
| 6,252,055 B1 | 6/2001 | Relton | |
| 6,503,510 B2 | 1/2003 | Koishihara et al. | |
| 6,699,974 B2 | 3/2004 | Ono et al. | |
| 2006/0286103 A1 * | 12/2006 | Kolhe et al. ................ | 424/143.1 |

FOREIGN PATENT DOCUMENTS

| | | | |
|---|---|---|---|
| EP | 0 239 400 B1 | 8/1994 | |
| EP | 1 090 643 A1 | 4/2001 | |
| EP | 1174048 A1 | 1/2002 | |
| JP | 58201994 B2 | 11/1993 | |
| JP | 11092399 A | 4/1999 | |
| JP | 11-510170 A | 9/1999 | |
| JP | 11-512753 A | 11/1999 | |
| JP | 2001503781 A | 3/2001 | |
| JP | 2002-504907 A | 2/2002 | |
| WO | 92/01047 A1 | 1/1992 | |
| WO | 92 03918 A1 | 3/1992 | |
| WO | 92 19759 A1 | 11/1992 | |
| WO | 92 20791 A1 | 11/1992 | |
| WO | 93 06213 A1 | 4/1993 | |
| WO | 93 11236 A1 | 6/1993 | |
| WO | 93 12227 A1 | 6/1993 | |
| WO | 93 19172 A1 | 9/1993 | |
| WO | 94 02602 A1 | 2/1994 | |
| WO | 94 25585 A1 | 11/1994 | |
| WO | 95 01438 A1 | 1/1995 | |
| WO | 95 15388 A1 | 6/1995 | |
| WO | 96 02576 A1 | 2/1996 | |
| WO | 96 33735 A1 | 10/1996 | |
| WO | 96 34096 A1 | 10/1996 | |
| WO | 97/04801 A1 | 2/1997 | |
| WO | 97/45140 A1 | 12/1997 | |
| WO | 98 13388 A1 | 4/1998 | |
| WO | 98 14580 A1 | 4/1998 | |
| WO | 98 19172 A1 | 5/1998 | |
| WO | 98 35698 A1 | 8/1998 | |
| WO | 98/56418 A1 | 12/1998 | |
| WO | WO 2004/019861 | * | 3/2004 |

OTHER PUBLICATIONS

Kirshnamurthy et al , Pharmaceutical Biotechnology, 2002, vol. 3, pp. 361-371.*
Lam et al. Journal of Pharmaceutical Sciences, 1997, vol. 86, No. 11, pp. 1250-1255.*
Borrebaeck, Carl A. K. et al, Table of Contents, Therapeutic Monoclonal Antibodies, 1990, MacMillan Publishers Inc., UK, pp. xi-xiii.
Galfre, G. et al, "Preparation of Monoclonal Antibodies: Strategies and Procedures", Method in Enzymology, vol. 73, 1981, pp. 3-46.
Sato, Koh et al., "Reshaping a Human Antibody to inhibit the Interleukin 6-dependent Tumor Cell Growth", Cancer Research, vol. 53, Feb. 15, 1993, pp. 851-856.
"Insoluble Particulate Matter Test for Injections", Japanese Phamacopoeia, JP XIV, Section 24, 45-47, 2001.
"Particulate Contamination: Visible Particles", European Phamacopoeia, Pharmaceutical Technical Procedures, Section 2.9. 20, 1997, pp. 151-152.

* cited by examiner

*Primary Examiner* — Elizabeth C Kemmerer
*Assistant Examiner* — Fozia Hamud
(74) *Attorney, Agent, or Firm* — Browdy and Neimark, PLLC

(57) ABSTRACT

An antibody-containing solution formulation comprising an organic acid and a surfactant as stabilizers; a method for suppressing the formation of visible insoluble matter and/or insoluble particles due to the presence of metal ions in an antibody-containing solution formulation, which comprises adding an organic acid to the solution; a method for suppressing the formation of visible insoluble matter and/or insoluble particles during shaking and freezing-thawing of an antibody-containing solution, which comprises adding a surfactant to the solution; and a method for stabilizing an antibody-containing solution, which comprises adding an organic acid and a surfactant.

9 Claims, No Drawings

ANTIBODY-CONTAINING SOLUTION FORMULATIONS

TECHNICAL FIELD

The present invention relates to stable solution formulations containing antibodies.

BACKGROUND ART

Advances in gene recombination technology have enabled the pharmaceutical use of antibodies such as immunoglobulins, monoclonal antibodies and humanized antibodies. To ensure a stable supply of these antibodies, it is necessary to establish production and storage conditions where the structure and activity of the antibodies can be maintained.

When proteins are stored in a highly concentrated solution form, they are usually associated with a problem of deterioration, including the formation of insoluble aggregates, which is required to be prevented. It is necessary to prevent such deterioration. For example, the applicant has found that an anti-HM1.24 antibody has a therapeutic effect on myeloma cells (JP KOKAI 11-092399), and also has studied formulation of this antibody. However, the anti-HM1.24 antibody is an unstable protein and is more likely to undergo physical and chemical changes (e.g., association, aggregation) as a result of stresses in the purification process. Such stresses include filtration stress during removal of virus and bacteria, concentration stress, heat stress and light stress.

Also, in the case of using genetic engineering techniques to obtain antibodies, antibody-producing cells are cultured in bulk, the antibody-containing solutions are purified, frozen and stored until thawing for use in drug formulation. However, repeating such shaking and freezing-thawing steps causes the formation of antibody aggregates and/or insoluble particles. Furthermore, long-term storage causes decomposition of antibodies, resulting in formation of decomposition products. These phenomena could eventually lead to a reduced level of antibodies remaining in the solution.

There is also a problem that visible insoluble matter and insoluble particles are formed in the presence of metal ions (Fe ions) introduced during the production process. Since metal ions (Fe ions), even when present in very small amounts in the solution, contribute to the formation of visible insoluble matter and insoluble particles, such ions should be removed completely. However, there is a limit to removal methods such as precipitation, complex formation, and so on. Thus, there has been a need to develop a strategy to avoid the formation of visible insoluble matter and insoluble particles even in the presence of metal ions.

Many attempts have been made to store proteins in a solution form, with the finding that stabilization effects are obtained by addition of a stabilizer for preventing chemical and physical changes. Examples of a stabilizer include high-molecular weight materials such as proteins (e.g., human serum albumin, purified gelatin) or low-molecular weight materials such as polyols, amino acids and surfactants. However, when added as stabilizers, organism-derived high-molecular weight materials like proteins are disadvantageous in that very complicated processes are required to remove contaminants, such as viruses and prions. With respect to low-molecular weight materials, it is also preferable to use them in as small amounts as possible.

For stabilization of lyophilized antibody formulations, there has been reported those comprising a sugar or amino sugar, an amino acid, and a surfactant as stabilizers (JP TOKUHYO 2001-503781).

However, there has been a strong demand for easy-to-use solution formulations that eliminates of dissolution and reconstitution steps before use. Especially, there has been a need for stable solution formulations containing antibodies.

DISCLOSURE OF THE INVENTION

The object of the present invention is to provide an antibody-containing solution formulation that is stable for long-term storage. This formulation is designed to suppress the formation of visible insoluble matter and/or insoluble particles, which are derived from the aggregation of antibodies caused by physical stresses (e.g., freezing-thawing) during its production process and by long-term storage; and to suppress the formation of visible insoluble matter and/or insoluble particles in the presence of metal ions (Fe ions) introduced during the production process.

As a result of extensive and intensive efforts made to achieve the above object, the inventors of the present invention have found that the use of organic acids significantly suppresses the formation of visible insoluble matter in the presence of iron, and that the addition of surfactants very significantly suppresses the formation of visible insoluble matter and/or insoluble particles during shaking and freezing-thawing steps. These findings have led to the completion of the present invention.

Namely, the present invention provides the following.
(1) An antibody-containing solution formulation comprising an organic acid and a surfactant as stabilizers.
(2) The solution formulation according to (1) above, wherein the organic acid is acetic acid or citric acid.
(3) The solution formulation according to (2) above, wherein the organic acid is acetic acid.
(4) The solution formulation according to (3) above, wherein the concentration of acetic acid is in the range of 10-50 mM.
(5) The solution formulation according to (1) above, wherein the surfactant is Polysorbate 80 or 20.
(6) The solution formulation according to (5) above, wherein the concentration of the surfactant is in the range of 0.01 to 10 mg/mL.
(7) The solution formulation according to (1) above, which further comprises sodium chloride.
(8) The solution formulation according to any one of (1) to (7) above, wherein the antibody is a recombinant antibody.
(9) The solution formulation according to (8) above, wherein the antibody is a chimeric antibody, a humanized antibody or a human antibody.
(10) The solution formulation according to (8) or (9) above, wherein the antibody is an antibody of IgG class.
(11) The solution formulation according to (10) above, wherein the antibody of IgG class is an antibody of IgG1 class.
(12) The solution formulation according to any one of (1) to (11) above, wherein the antibody is an anti-interleukin-6 receptor antibody or an anti-HM1.24 antibody.
(13) The solution formulation according to (12) above, wherein the antibody is an anti-HM1.24 antibody.
(14) An anti-HM1.24 antibody-containing solution formulation comprising 10-50 mM of acetic acid and 0.01-10 mg/mL of Polysorbate 80 as stabilizers.
(15) A method for suppressing formation of visible insoluble matter and/or insoluble particles caused by metal ions presented in an antibody-containing solution formulation, which comprises adding an organic acid to the solution.
(16) A method for suppressing formation of visible insoluble matter and/or insoluble particles during shaking and freezing-thawing of an antibody-containing solution, which comprises adding a surfactant to the solution.

(17) A method for stabilizing an antibody-containing solution, which comprises adding an organic acid and a surfactant.

BEST MODE FOR CARRYING OUT THE INVENTION

As used herein, the term "antibody-containing solution formulation" is intended to mean a solution formulation containing an antibody as an active ingredient and available for use in administration to animals including human, preferably prepared without using a lyophilization step.

As used herein, the term "antibody-containing solution" is intended to mean a solution containing any antibody, whether the antibody is native one or recombinant one. It is preferably a culture medium of mammalian cells (e.g., CHO cells) containing antibody molecules produced by culture, which may further be subjected to partial purification or other certain treatment(s) (bulk solution), or alternatively, the above-stated solution formulation available for use in administration to animals including human.

As used herein, the term "insoluble particles" is intended to mean insoluble particulate matter of 10 μm or larger, as defined in Test for Insoluble Particles in Injections, Standard Test Procedures, the Japanese Pharmacopoeia. The measurement of insoluble particles may be accomplished by using a microscope, a filter for collecting insoluble particles and a membrane filter for measurement, but conveniently by using a light shielding type of an automatic particle analyzer.

As used herein, the term "visible insoluble matter" is intended to mean those easily detected by the unaided eye when a solution formulation in a container is placed directly under a white light at a brightness of about 3000 lux (2000 to 3750 lux) against a black background, in accordance with the procedures described in Section 2.9.20 of the European Pharmacopoeia, third edition.

As used herein, the terms "aggregation products" and "decomposition products" are intended to mean aggregates and fragments, respectively, of antibody molecules used as an active ingredient of the formulation. The content of these products may be determined, for example, on the basis of peak ratio with gel permeation chromatography as stated below.

There is no particular limitation on the antibodies used in the solution formulation/of the present invention, as long as they can bind to a desired antigen. It is possible to use mouse antibodies, rat antibodies, rabbit antibodies, sheep antibodies, chimeric antibodies, humanized antibodies, human antibodies and the like, as appropriate. Such antibodies may be polyclonal or monoclonal, but are preferably monoclonal because uniform antibody molecules can be produced stably. Polyclonal and monoclonal antibodies can be prepared in a manner well known to those skilled in the art.

In principle, monoclonal antibody-producing hybridomas can be prepared using known techniques, as follows. Namely, a desired antigen or a desired antigen-expressing cell is used as a sensitizing antigen and immunized in accordance with conventional procedures for immunization. The resulting immunocytes are then fused with known parent cells using conventional procedures for cell fusion, followed by selection of monoclonal antibody-producing cells (hybridomas) through conventional screening procedures. Preparation of hybridomas may be accomplished according to, for example, the method of Milstein et al. (Kohler, G. and Milstein, C., Methods Enzymol. (1981) 73:3-46). If an antigen used is less immunogenic, such an antigen may be conjugated with an immunogenic macromolecule (e.g., albumin) before use in immunization.

In addition, antibody genes are cloned from hybridomas, integrated into appropriate vectors, and then transformed into hosts to produce antibody molecules using gene recombination technology. The genetically recombinant antibodies thus produced may also be used in the present invention (see, e.g., Carl, A. K. Borrebaeck, James, W. Larrick, THERAPEUTIC MONOCLONAL ANTIBODIES, Published in the United Kingdom by MACMILLAN PUBLISHERS LTD, 1990). More specifically, cDNA of antibody variable domains (V domains) is synthesized from hybridoma mRNA using reverse transcriptase. Upon obtaining DNA encoding the target antibody V domains, the DNA is ligated to DNA encoding desired antibody constant domains (C domains) and integrated into an expression vector. Alternatively, the DNA encoding the antibody V domains may be integrated into an expression vector carrying the DNA of the antibody C domains. The DNA construct is integrated into an expression vector such that it is expressed under control of an expression regulatory region, e.g., an enhancer or a promoter. Host cells are then transformed with this expression vector for antibody expression.

In the present invention, it is possible to use genetically recombinant antibodies (e.g., chimeric antibodies, humanized antibodies) that are artificially modified with a view to attenuating the characteristics as heteroantigen to human. These modified antibodies may be prepared in a known manner. A chimeric antibody is composed of variable domains of heavy and light chains from a non-human mammalian (e.g., mouse) antibody and constant domains of heavy and light chains from a human antibody. To obtain chimeric antibodies, DNAs encoding such mouse antibody variable domains may be ligated to DNAs encoding the human antibody constant domains, and then integrated into an expression vector, followed by transformation into a host for antibody production.

Humanized antibodies are also called reshaped human antibodies and are obtained by grafting complementarity determining regions (CDRs) of non-human mammalian (e.g., mouse) antibodies to replace those of human antibodies. Standard gene recombination procedures for this purpose are also known. More specifically, a DNA sequence designed to allow ligation between CDRs of mouse antibody and framework regions (FRs) of human antibody is synthesized by PCR from several oligonucleotides which are prepared to have sections overlapping with one another at the ends. The DNA thus obtained is ligated to DNA encoding human antibody constant domains, and integrated into an expression vector, followed by transformation into a host for antibody production (see European Patent Publication No. EP 239400 and International Patent Publication No. WO 96/02576). The FRs of human antibody, which is ligated to CDRs, are selected such that the complementarity determining regions form a favorable antigen-binding site. If necessary, amino acid substitutions may be made in the framework regions of antibody variable domains such that the complementarity determining regions of reshaped humanized antibody may form an appropriate antigen-binding site (Sato, K. et al., Cancer Res. (1993) 53, 851-856).

Procedures for obtaining human antibodies are also known. For example, human lymphocytes are sensitized in vitro with a desired antigen or a desired antigen-expressing cell, and the sensitized lymphocytes are then fused with human myeloma cells (e.g., U266) to give desired human antibodies having binding activity to the antigen (see JP KOKOKU 01-59878). Alternatively, transgenic animals having the entire repertoires of human antibody genes may be immunized with an antigen to obtain desired human antibodies (see International Publication Nos. WO 93/12227, WO 92/03918, WO 94/02602, WO 94/25585, WO 96/34096 and WO 96/33735). There are additional techniques using human antibody libraries to give human antibodies by panning. For example, human antibody variable domains may be expressed by phage display technology as a single-chain antibody (scFv) on the surface of phages, followed by selection of phages binding to the antigen. When genes of the selected phages are analyzed, it is possible to determine DNA sequences encoding human antibody variable domains binding to the antigen. Once the DNA sequences of scFv binding to the antigen have been identified, the sequences may be used to construct appropriate expression vectors to obtain human antibodies. These techniques are already well known and can be found in WO 92/01047, WO 92/20791, WO 93/06213, WO 93/11236, WO 93/19172, WO 95/01438 and WO 95/15388.

In a case where antibody genes are isolated and then transformed into appropriate hosts to produce antibodies, any suitable combination of host and expression vector can be used for this purpose. When eukaryotic cells are used as hosts, animal cells, plant cells and fungal cells may be used. Animal cells known for this purpose include (1) mammalian cells such as CHO, COS, myeloma, BHK (baby hamster kidney), HeLa and Vero, (2) amphibian cells such as *Xenopus* oocytes, and (3) insect cells such as sf9, sf21 and Tn5. Plant cells include those derived from *Nicotiana* plants (e.g., *Nicotiana tabacum*), which may be subjected to callus culture. Fungal cells include yeasts such as *Saccharomyces* (e.g., *Saccharomyces serevisiae*) and filamentous fungi such as *Aspergillus* (e.g., *Aspergillus niger*). When prokaryotic cells are used, there are production systems employing bacterial cells. Bacterial cells known for this purpose are *E. coli* and *Bacillus subtilis*. Antibodies can be obtained by introducing target antibody genes into these cells via transformation and then culturing the transformed cells in vitro.

Examples of antibodies to be contained in the stabilized formulation of the present invention include, but are not limited to, an anti-IL-6 receptor antibody, an anti-HM1.24 antigen monoclonal antibody and an anti-parathyroid hormone-related peptide antibody (anti-PTHrP antibody).

Examples of reshaped humanized antibodies preferred for use in the present invention include a humanized anti-IL-6 receptor antibody (hPM-1) (see International Publication No. WO92-19759), a humanized anti-HM1.24 antigen monoclonal antibody (see International Publication No. WO98-14580) and a humanized anti-para thyroid hormone-related peptide antibody (anti-PTHrP antibody; see International Publication No. WO98-13388).

Antibodies to be contained in the solution formulation of the present invention may be of any immunoglobulin class, preferably of IgG class including IgG1, IgG2, IgG3 and IgG4, and more preferably of IgG1 class.

In the antibody-containing solution or solution formulation of the present invention, the formation of visible insoluble matter and/or insoluble particles, which is caused by metal ions (Fe ions) introduced during production procedures, can be significantly suppressed by addition of an organic acid. Preferred organic acids are acetic acid and citric acid, with acetic acid being more preferred. Such acids may be used in combination.

Addition of an organic acid(s) may be accomplished by dissolving an antibody and other ingredients in an organic acid buffer. To prepare a solution formulation, an antibody and other ingredients may be dissolved in an aqueous buffer known in the art of solution formulations, including acetate buffer and/or citrate buffer (preferably sodium citrate buffer). The concentration of the buffer used is usually 1 to 500 mM, preferably 5 to 100 mM, and more preferably 10 to 50 mM.

Due to inclusion of an organic acid, the antibody-containing solution formulation of the present invention achieved significant suppression of insoluble contaminant formation, even in the presence of Fe ions during storage at room temperature (25° C.), as compared to an antibody-containing solution formulation supplemented with an inorganic acid.

In the present invention, addition of a surfactant allows very significant suppression of visible insoluble matter and/or insoluble particle formation during shaking and freezing-thawing of the antibody-containing solution formulation. Typical examples of a surfactant include:

nonionic surfactants (HLB 6 to 18) such as sorbitan fatty acid esters (e.g., sorbitan monocaprylate, sorbitan monolaurate, sorbitan monopalmitate), glycerine fatty acid esters (e.g., glycerine monocaprylate, glycerine monomyristate, glycerine monostearate), polyglycerine fatty acid esters (e.g., decaglyceryl monostearate, decaglyceryl distearate, decaglyceryl monolinoleate), polyoxyethylene sorbitan fatty acid esters (e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g., polyoxyethylene sorbitol tetrastearate, polyoxyethylene sorbitol tetraoleate), polyoxyethylene glycerine fatty acid esters (e.g., polyoxyethylene glyceryl monostearate), polyethylene glycol fatty acid esters (e.g., polyethylene glycol distearate), polyoxyethylene alkyl ethers (e.g., polyoxyethylene lauryl ether), polyoxyethylene polyoxypropylene alkyl ethers (e.g., polyoxyethylene polyoxypropylene glycol, polyoxyethylene polyoxypropylene propyl ether, polyoxyethylene polyoxypropylene cetyl ether), polyoxyethylene alkylphenyl ethers (e.g., polyoxyethylene nonylphenyl ether), polyoxyethylene hydrogenated castor oils (e.g., polyoxyethylene castor oil, polyoxyethylene hydrogenated castor oil), polyoxyethylene beeswax derivatives (e.g., polyoxyethylene sorbitol beeswax), polyoxyethylene lanolin derivatives (e.g., polyoxyethylene lanolin), and polyoxyethylene fatty acid amides (e.g., polyoxyethylene stearic acid amide);

anionic surfactants such as $C_{10}$-$C_{18}$ alkyl sulfate (e.g., sodium cetyl sulfate, sodium lauryl sulfate, sodium oleyl sulfate), polyoxyethylene $C_{10}$-$C_{18}$ alkyl ether sulfate with an average of 2 to 4 moles of ethylene oxide units added (e.g., sodium polyoxyethylene lauryl sulfate), and $C_8$-$C_{18}$ alkyl sulfosuccinate ester salts (e.g., sodium lauryl sulfosuccinate ester); and natural surfactants such as lecithin, glycerophospholipid, sphingophospholipids (e.g., sphingomyelin), and sucrose esters of $C_{12}$-$C_{18}$ fatty acids. The formulation of the present invention may be supplemented with one or more of these surfactants. Preferred surfactants for use in the solution formulation of the present invention are polyoxyethylene sorbitan fatty acid esters such as Polysorbate 20, 40, 60 or 80, with Polysorbate 20 and 80 being particularly preferred. Also preferred is polyoxyethylene polyoxypropylene glycol typified by poloxamers (e.g., Pluronic F-68®), with Poloxamer 188 being particularly preferred.

The amount of a surfactant to be added will vary depending on the type of surfactant used. In the case of Polysorbate 20 or Poloxamer 188, it is usually added in an amount of 0.001 to 100 mg/mL (0.0001% to 10%), preferably 0.005 to 50 mg/mL (0.0005% to 5%), and more preferably 0.01 to 10 mg/mL (0.001% to 1%). Even more preferably, the amount is 0.025 to 0.25 mg/mL (0.0025% to 0.025%) at which the maximum number of insoluble particles having a diameter of no less than 25 μm can be of no greater than 3 even after shaking (200 strokes/min×30 minutes) and one cycle of freezing-thawing (−80° C./25° C.). In the case of Polysorbate 80, it is usually added in an amount of 0.001 to 100 mg/mL (0.0001% to 10%), preferably 0.005 to 50 mg/mL (0.0005% to 5%), and more preferably 0.01 to 10 mg/mL (0.001% to 1%). Even more preferably, the amount is 0.025 to 1 mg/mL (0.0025% to 0.1%) at which the maximum number of insoluble particles having a diameter of no less than 25 μm can be zero, and no formation of visible insoluble matter is observed even after shaking (200 strokes/min×60 minutes) and 3 cycles of freezing-thawing (−20° C./5° C.).

Preferably, the antibody-containing solution formulation of the present invention is substantially free from protein stabilizers such as human serum albumin and purified gelatin.

The antibody-containing solution formulation of the present invention may further comprise sodium chloride in an amount of 10 to 300 mM, preferably 20 to 200 mM.

The antibody-containing solution formulation of the present invention preferably has a pH of 4 to 8, more preferably 5 to 7.5. However, the pH will vary depending on the type of antibody contained and is not limited to this range. For example, in the case of using an anti-HM1.24 antibody, a pH range of 5.5 to 6.5 is most preferred for the purpose of avoiding aggregation induced by heat stress, maintaining a high residue level, and suppressing the formation of charged heteromolecules (including deamidated products, etc.). The pH preferred for each antibody may be determined in accordance with the examples shown below.

The formulation of the present invention may further comprise, as a stabilizer, sugar alcohols such as mannitol and sorbitol or saccharides such as nonreducing oligosaccharides including nonreducing disaccharides (e.g., sucrose, trehalose) and nonreducing trisaccharides (e.g., raffinose).

Likewise, the formulation of the present invention may further comprise, as an isotonizing agent, polyethylene glycol or saccharides such as dextran, mannitol, sorbitol, inositol, glucose, fructose, lactose, xylose, mannose, maltose, sucrose, trehalose and raffinose.

If desired, the antibody-containing solution formulation of the present invention may further comprise a diluent, a solubilizer, an excipient, a pH adjuster, a soothing agent, a buffer, a sulfur-containing reducing agent, an antioxidant and the like. For instance, examples of a sulfur-containing reducing agent include those having a sulfhydryl group such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a $C_1$-$C_7$ thioalkanoic acid. Examples of an antioxidant include erythorbic acid, dibutylhydroxytoluene, butylhydroxyanisole, α-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, the formulation of the present invention may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The antibody-containing solution formulation of the present invention is usually administered by parenterally, for example, in the dosage form of injections (e.g., subcutaneous, intravenous, intramuscular or intraperitoneal injections) as well as transdermal, transmucosal, transnasal and transpulmonary preparations. However, it may also be administered orally.

The antibody-containing solution formulation of the present invention can usually be provided in the form of containers having a definite volume, including sealed and sterilized plastic or glass vials, ampoules and syringes, as well as in the form of large volume containers like bottles. In terms of convenience of handling, pre-filled syringes are preferred.

The amount of an antibody in the formulation of the present invention can be determined as appropriate for the type and severity of disease to be treated, the age of a patient, etc. In general, an antibody is incorporated in an amount of 0.1 to 200 mg/ml, preferably 1 to 120 mg/ml.

As shown in the examples below, the antibody-containing solution formulation of the present invention was confirmed to significantly suppress the formation of visible insoluble matter in the presence of iron when an organic acid, particularly acetic acid and/or citric acid, was added to an antibody solution. Thus, addition of an organic acid significantly suppressed the formation of visible insoluble matter and/or insoluble particles, which was caused by metal ions (Fe ions) introduced during production procedures. When further supplemented with a surfactant, the antibody-containing solution formulation of the present invention achieved very significant suppression of visible insoluble matter and/or insoluble particle formation induced by shaking and freezing-thawing.

The present invention will now be further described in the following examples, which are not intended to limit the scope of the invention. Based on the detailed description, various changes and modifications will be apparent to those skilled in the art, and such changes and modifications fall within the scope of the invention.

EXAMPLES

Antibody Samples

A humanized anti-HM1.24 antigen monoclonal antibody (hereinafter referred to as the "anti-HM1.24 antibody") was produced in accordance with Reference Example 2 of International Publication No. WO98-35698 and used in the examples.

The anti-HM1.24 antibody used in the examples was of IgG1 class.

Test Procedures (1) Gel Permeation Chromatography (GPC)

Aggregation and decomposition products of the antibody are separated by differences in molecular weight. In this test, dimers, trimers and higher aggregates of the antibody are collectively referred to as aggregation products, while two low-molecular-weight fragments generated from the antibody are referred to as decomposition product 1 and decomposition product 2, respectively. The residue level of the main peak was also taken into consideration.

The content was evaluated as the residue level based on the initial level. Aggregation and decomposition products were both expressed in percent (%).

GPC Conditions
  Column: TSK gel G3000SWXL (TOSOH)
  Guard column: TSK guard column SWXL (TOSOH)
  Column temperature: kept constant around 25° C.
  Mobile phase: 50 mM phosphate buffer (pH 7.0)/300 mM sodium chloride
  Flow rate: about 0.5 mL/min
  Detection wavelength: 280 nm Calculation of Concentration Concentration of anti-HM1.24 antibody (mg/mL)
(concentration of standard sample×peak area of
anti-HM1.24 antibody×amount of standard
sample injected)/(total peak area of standard
sample×amount of test substance injected)

Residual level of anti-HM1.24 antibody (%)=[(anti-
HM1.24 antibody content after stress)/(initial
anti-HM1.24 antibody content)]×100

Aggregation products (also for decomposition prod-
ucts) (%)=[(peak area of aggregation (cleavage)
products)/(total peak area)]×100

(2) Ion Exchange Chromatography (IEC)

Charged heteromolecules are separated, which are generated by deterioration including deamidation of the antibody. Stability was evaluated by changes in main peak area.

HPLC Conditions
  Column: Poly CAT A (PolyLC Inc.)
  Guard column: Poly CAT A Javelin guard (PolyLC Inc.)
  Column temperature: kept constant around 25° C.
  Flow rate: 1 mL/min
  Detection wavelength: 280 nm
  Mobile phase: using a gradient of the following two eluents A and B:
    Eluent A: 25 mM MES buffer (0.05% sodium azide, pH 6.1)
    Eluent B: 250 mM sodium chloride in 25 mM MES buffer (0.05% sodium azide, pH 6.1)

Measurement

The column was equilibrated with 30% Eluent B and then injected with a sample solution. A linear gradient was run to 70% Eluent B over 32 minutes, followed by maintaining 70% Eluent B for 5 minutes. After washing with 100% Eluent B for 5 minutes or longer, the column was equilibrated with 30% Eluent B for 15 minutes or longer and provided for the next measurement.

Analysis

Peak areas of the resulting HPLC chromatogram were analyzed by automatic integration to determine the percentage of the main peak area.

(3) Insoluble Particle Test

Measurement: according to the test for insoluble particles in injections using a light shielding type of an automatic particle analyzer, as described in Standard Test Procedures of the Japanese Pharmacopoeia.

Instrument: a light shielding type of an automatic particle analyzer (HIAC)

(4) Foreign Insoluble Matter Test

Measurement: Visible insoluble matter was detected by the unaided eye against a black background according to the procedures in Section 2.9.20 of the European Pharmacopoeia, third edition.

Example 1

Effects of Organic Acid Addition

Anti-HM1.24 antibody formulations prepared in different buffers (phosphate, acetate, citrate) were supplemented with iron ($FeCl_3$), and observed for the formation of visible insoluble matter by the unaided eye against a black background in accordance with the foreign insoluble matter test. The samples were stored at room temperature (about 25° C.). Table 1 summarizes the composition of tested formulations, and Table 2 shows the results obtained.

TABLE 1

Composition of tested formulations

| | Sample No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Anti-HM1.24 antibody (mg/mL) | 2.5 | 2.5 | 2.5 | 2.5 | 2.5 | 2.5 | 2.5 | 2.5 | 2.5 | 2.5 | 2.5 | 2.5 |
| Polysorbate 80 (%) | 0.025 | 0.025 | 0.025 | 0.025 | 0.025 | 0.025 | 0.025 | 0.025 | 0.025 | 0.025 | 0.025 | 0.025 |
| Buffer type | Ac | Ac | Ac | Ac | Phos | Phos | Phos | Phos | Cit | Cit | Cit | Cit |
| Buffer conc. (mM) | 20 | 20 | 20 | 20 | 20 | 20 | 20 | 20 | 20 | 20 | 20 | 20 |
| Sodium chloride (mM) | 100 | 100 | 100 | 100 | 100 | 100 | 100 | 100 | 100 | 100 | 100 | 100 |
| pH | 6.0 | 6.0 | 6.0 | 6.0 | 6.0 | 6.0 | 6.0 | 6.0 | 6.0 | 6.0 | 6.0 | 6.0 |
| $FeCl_3$ conc. (µg/L) | 0 | 10 | 100 | 1000 | 0 | 10 | 100 | 1000 | 0 | 10 | 100 | 1000 |

Ac: acetate buffer,
Phos: phosphate buffer,
Cit: citrate buffer

TABLE 2

Results of foreign insoluble matter test on samples supplemented with iron ($FeCl_3$)

| Sample No. | Buffer | Conc. | Initial | 1 day | 4 days | 5 days | 6 days | 7 days | 8 days |
|---|---|---|---|---|---|---|---|---|---|
| 1 | Acetate | 0 µg/L | − | − | − | − | − | ± | − |
| 2 | | 10 µg/L | − | − | ± | ± | + | ± | + |
| 3 | | 100 µg/L | − | − | ± | ± | ± | ± | + |
| 4 | | 1000 µg/L | − | − | ± | ± | ± | ± | + |
| 5 | Phosphate | 0 µg/L | − | − | − | − | − | − | − |

TABLE 2-continued

Results of foreign insoluble matter test on samples supplemented with iron (FeCl$_3$)

| Sample No. | Buffer | Conc. | Initial | 1 day | 4 days | 5 days | 6 days | 7 days | 8 days |
|---|---|---|---|---|---|---|---|---|---|
| 6 |  | 10 μg/L | – | ± | ± | ± | ± | + | ± |
| 7 |  | 100 μg/L | – | – | ± | + | + | + | + |
| 8 |  | 1000 μg/L | – | – | ++ | ++ | ++ | +++ | +++ |
| 9 | Citrate | 0 μg/L | – | – | – | – | – | – | ± |
| 10 |  | 10 μg/L | – | – | – | – | – | ± | + |
| 11 |  | 100 μg/L | – | – | – | – | ± | ± | + |
| 12 |  | 1000 μg/L | – | – | – | – | – | ± | ± |

(Evaluation)
not observed ⟶ highly observed
(–) < (±) < (+) < (++) < (+++)

As is evident from the above results, the anti-HM1.24 antibody formulations prepared in acetate and citrate buffers significantly suppressed the formation of visible insoluble matter in the presence of iron, as compared to the formulation prepared in phosphate buffer.

Example 2

Effects of Surfactant Addition

Polysorbate 80, Polysorbate 20 and Poloxamer 188 were used in the shaking test, freezing-thawing test and storage stability test of anti-HM1.24 antibody formulations (2.5 to 10 mg/mL) to study surfactant-induced effects on the formulations.

(1) Physical Stress Test

Surfactant-induced effects on physical stresses (shaking and freezing-thawing) were studied in terms of insoluble particle or visible insoluble matter formation.

(1-1) Test on 2.5 mg/mL Solutions

The evaluation was conducted as follows. Table 3 shows the composition of tested formulations along with the results obtained.

Test sample: 2 mL per 5 mL vial (Samples 13-22)

Evaluation: insoluble particle test using a light shielding type of an automatic particle analyzer (HIAC)

Evaluation Conditions:

(i) Shaking Test

Shaking conditions: 200 strokes/min.×30 min.

Shaker: RECIPRO SHAKER SR-I (Taiyo Scientific Industrial Co., Ltd.)

(ii) Freezing-Thawing Test

Freezing-thawing conditions: −80° C.→25° C.×1 cycle

TABLE 3

Composition of tested formulations and results

|  |  | Sample No. | | | | | | | | | |
|---|---|---|---|---|---|---|---|---|---|---|---|
|  |  | 13 | 14 | 15 | 16 | 17 | 18 | 19 | 20 | 21 | 22 |
| Anti-HM1.24 antibody (mg/mL) |  | 2.5 | 2.5 | 2.5 | 2.5 | 2.5 | 2.5 | 2.5 | 2.5 | 2.5 | 2.5 |
| Polysorbate 80 (%) |  | 0.025 | 0.01 | 0.0025 | — | — | — | — | — | — | — |
| Polysorbate 20 (%) |  | — | — | — | 0.025 | 0.01 | 0.0025 | — | — | — | — |
| Poloxamer 188 (%) |  | — | — | — | — | — | — | 0.025 | 0.01 | 0.0025 | — |
| Sodium chloride (mM) |  | 100 | 100 | 100 | 100 | 100 | 100 | 100 | 100 | 100 | 100 |
| Acetate buffer (mM) |  | 20 | 20 | 20 | 20 | 20 | 20 | 20 | 20 | 20 | 20 |
| PH |  | 60 | 6.0 | 6.0 | 6.0 | 6.0 | 6.0 | 6.0 | 6.0 | 6.0 | 6.0 |
| Initial counts of particles | ≥10 μm | 2 | 9 | 6 | 6 | 9 | 3 | 9 | 1 | 5 | 19 |
| (Counts/mL) | ≥25 μm | 0 | 1 | 0 | 0 | 0 | 0 | 0 | 0 | 0 | 0 |
| After shaking | ≥10 μm | 78 | 49 | 30 | 66 | 89 | 74 | 131 | 32 | 44 | 5922 |
| (Counts/mL) | ≥25 μm | 3 | 1 | 0 | 1 | 1 | 0 | 1 | 0 | 1 | 1485 |
| After freezing-thawing | ≥10 μm | 6 | 1 | 2 | 3 | 2 | 2 | 3 | 2 | 4 | 329 |
| (Counts/mL) | ≥25 μm | 1 | 0 | 0 | 2 | 0 | 0 | 0 | 2 | 1 | 47 |

The surfactants used (Polysorbate 80, Polysorbate 20, Poloxamer 188) were found to produce a significant effect when added in the range of 0.0025% to 0.025%, in view of suppression of the formation of insoluble particles or visible insoluble matter.

(1-2) Test on 10 mg/mL Solutions

The evaluation was conducted as follows. Table 4 shows the composition of tested formulations along with the results obtained.

Test sample: 10 mL per 20 mL vial (Samples 23-28)

Evaluation:
(i) Insoluble particle test using a light shielding type of an automatic Particle Analyzer (HIAC)
(ii) Insoluble contamination test according to the EP Method (against a black background)

Evaluation Conditions:

(i) Shaking Test
  Shaking conditions: 200 strokes/min.×60 min.
  Shaker: RECIPRO SHAKER SR-I
  (Taiyo Scientific Industrial Co., Ltd.)
(ii) Freezing-Thawing Test
  Freezing-thawing conditions: −20° C.⇔ 5° C.×3 cycles

TABLE 4

Composition of tested formulations and results

| | | | Sample No. | | | | | |
|---|---|---|---|---|---|---|---|---|
| | | | 23 | 24 | 25 | 26 | 27 | 28 |
| Anti-HM1.24 antibody (mg/mL) | | | 10 | 10 | 10 | 10 | 10 | 10 |
| Polysorbate 80 (%) | | | 0 | 0.00025 | 0.0025 | 0.025 | 0.05 | 0.1 |
| Acetic acid (mM) | | | 10 | 10 | 10 | 10 | 10 | 10 |
| Sodium chloride (mM) | | | 100 | 100 | 100 | 100 | 100 | 100 |
| PH | | | 6.0 | 6.0 | 6.0 | 6.0 | 6.0 | 6.0 |
| Initial counts of particles | ≥10 μm | | 2 | 0 | 0 | 0 | 1 | 0 |
| (Counts/mL) | ≥25 μm | | 0 | 0 | 0 | 0 | 0 | 0 |
| After shaking | ≥10 μm | | 44079 | 0 | 0 | 0 | 0 | 4 |
| (Counts/mL) | ≥25 μm | | 15699 | 0 | 0 | 0 | 0 | 0 |
| After freezing-thawing | ≥10 μm | | 5054 | 1 | 0 | 0 | 0 | 0 |
| (×3 cycles) (Counts/mL) | ≥25 μm | | 333 | 0 | 0 | 0 | 0 | 0 |
| Insoluble contamination test | Initial | | − | − | − | − | − | − |
| | Shaken | | + | − | − | − | − | − |
| | Frozen-thawed (×3 times) | | + | + | − | − | − | − |

+: observed,
−: not observed

Polysorbate 80 was found to produce an effect when added in the range of 0.0025% to 0.1%, in view of suppression of the formation of visible insoluble matter and insoluble particles.

(2) Storage Stability Test

Polysorbate 80 was tested for its inhibitory effect on the time-dependent formation of visible insoluble matter in anti-HM1.24 antibody solutions during storage at 5° C.

(2-1) Test on 2.5 and 5.0 mg/mL Solutions

The evaluation was conducted as follows. Table 5 shows the composition of tested formulations along with the results obtained.

Test sample: 5 mL per 10 mL vial (Samples 29-38)
Evaluation: insoluble contamination test according to the EP method (against a black background)
Storage conditions: at 5° C. for 3 months (5° C.-3M)

TABLE 5

Composition of tested formulations and results

| | | Sample No. | | | | | | | | |
|---|---|---|---|---|---|---|---|---|---|---|
| | | 29 | 30 | 31 | 32 | 33 | 34 | 35 | 36 | 37 | 38 |
| Anti-HM1.24 antibody (mg/mL) | | 2.5 | 2.5 | 2.5 | 2.5 | 2.5 | 5.0 | 5.0 | 5.0 | 5.0 | 5.0 |
| Polysorbate 80 (%) | | — | 0.001 | 0.0025 | 0.01 | 0.025 | — | 0.002 | 0.005 | 0.02 | 0.05 |
| Sodium chloride (mM) | | 100 | 100 | 100 | 100 | 100 | 100 | 100 | 100 | 100 | 100 |
| Acetate buffer (mM) | | 20 | 20 | 20 | 20 | 20 | 20 | 20 | 20 | 20 | 20 |
| PH | | 6.0 | 6.0 | 6.0 | 6.0 | 6.0 | 6.0 | 6.0 | 6.0 | 6.0 | 6.0 |
| Vial ID1 | Initial | − | − | − | − | − | + | − | − | − | − |
| | 3M | + | + | − | − | − | ++ | − | − | − | − |

TABLE 5-continued

Composition of tested formulations and results

| | | Sample No. | | | | | | | | | |
|---|---|---|---|---|---|---|---|---|---|---|---|
| | | 29 | 30 | 31 | 32 | 33 | 34 | 35 | 36 | 37 | 38 |
| Vial ID2 | Initial | – | – | – | – | – | – | – | – | – | – |
| | 3M | + | – | – | – | – | ++ | – | – | – | + |
| Vial ID3 | Initial | ++ | – | – | – | – | – | – | – | – | – |
| | 3M | + | + | + | – | – | ++ | – | – | + | – |
| Vial ID4 | Initial | – | – | – | – | – | – | – | – | – | – |
| | 3M | + | + | – | – | – | ++ | + | + | – | – |
| Vial ID5 | Initial | – | – | – | – | – | – | – | – | – | – |
| | 3M | + | – | – | – | – | ++ | + | – | – | – |

++: highly observed,
+: slightly observed,
–: not observed

After storage at 5° C. for 3 months, a remarkable formation of visible insoluble matter was observed in the formulations containing no Polysorbate 80 (Samples 29 and 34), whereas a significant inhibitory effect on formation of contamination was observed when Polysorbate 80 was added to the formulations in the range of 0.001% to 0.05%.

(2-2) Test on 10 mg/mL Solutions

The evaluation was conducted as follows. Table 6 shows the composition of tested formulations along with the results obtained.

Test sample: 10 mL per 20 mL vial (Samples 39-42)
Evaluation: foreign insoluble matter test according to the EP method (against a black background)
Storage conditions: at 5° C. for 3, 6 and 12 months (5° C.-3, 6, 12M)

TABLE 6

Composition of tested formulations and results

| | | Sample No. | | | |
|---|---|---|---|---|---|
| | | 39 | 40 | 41 | 42 |
| Anti-HM1.24 antibody (mg/mL) | | 10 | 10 | 10 | 10 |
| Polysorbate 80 (%) | | 0 | 0.005 | 0.025 | 0.05 |
| Sodium chloride (mM) | | 100 | 100 | 100 | 100 |
| Acetate buffer (mM) | | 10 | 10 | 10 | 10 |
| PH | | 6.0 | 6.0 | 6.0 | 6.0 |
| Foreign insoluble matter test | Initial | – | – | – | – |
| | 5° C.-3M | + | – | – | – |
| | 5° C.-6M | + | – | – | – |
| | 5° C.-12M | + | – | – | – |

+: observed,
–: not observed

When added at 0.005% or more, Polysorbate 80 was found to produce a significant effect on the formation of visible insoluble matter.

Example 3

Dependency on pH

To confirm the optimum pH for the anti-HM1.24 antibody in the concentration range of 2.5 to 10 mg/mL, the heat resistance test and the storage stability test were conducted.

(1) Test on 2.5 mg/mL Formulations

The evaluation was conducted as follows. Tables 7 and 8 show the composition of tested formulations and the results obtained, respectively.

Test sample: 1 mL per 5 mL vial (Samples 43-47)
Evaluation: heat resistance test, storage stability test
Storage conditions: at 50° C. for 3 moths (50° C.-3M) (GPC) at 5° C. for 6 months (5° C.-6M) (IEC)

TABLE 7

Composition of tested formulations

| | Sample No. | | | | |
|---|---|---|---|---|---|
| | 43 | 44 | 45 | 46 | 47 |
| Anti-HM1.24 antibody (mg/mL) | 2.5 | 2.5 | 2.5 | 2.5 | 2.5 |
| Acetate buffer (mM) | 20 | 20 | 20 | 20 | 20 |
| Sodium chloride (mM) | 100 | 100 | 100 | 100 | 100 |
| Polysorbate 80 (%) | 0.025 | 0.025 | 0.025 | 0.025 | 0.025 |
| PH | 5.0 | 5.5 | 6.0 | 6.5 | 7.0 |

TABLE 8

Evaluation results of heat resistance test (50° C.-3M) and storage stability test (5° C.-6M)

| | | GPC (50° C.-3M) | | | | |
|---|---|---|---|---|---|---|
| Sample No. | pH | Residue (%) | Aggregation products (%) | Decomposition product 1 (%) | Decomposition product 2 (%) | IEC (5° C.-6M) Main peak (%) |
| 43 | 5.0 | 53.7 | 35.8 | ND | 12.6 | 93.1 |
| 44 | 5.5 | 68.1 | 29.6 | ND | 9.5 | 92.8 |
| 45 | 6.0 | 76.6 | 19.6 | 4.9 | 8.2 | 92.5 |

TABLE 8-continued

Evaluation results of heat resistance test (50° C.-3M) and storage stability test (5° C.-6M)

| Sample No. | pH | Residue (%) | GPC (50° C.-3M) Aggregation products (%) | Decomposition product 1 (%) | Decomposition product 2 (%) | IEC (5° C.-6M) Main peak (%) |
|---|---|---|---|---|---|---|
| 46 | 6.5 | 78.2 | 15.2 | 8.9 | 7.8 | 90.7 |
| 47 | 7.0 | 77.8 | 12.4 | 11.4 | 8.5 | 88.0 |

(2) Test on 10 mg/mL Formulations

The evaluation was conducted as follows. Tables 9 and 10 show the composition of tested formulations and the results obtained, respectively.
Test sample: 1 mL per 5 mL vial (Samples 48-54)
Evaluation: heat resistance test
Storage conditions: at 50° C. for 1 month (50° C.-1M) (GPC)
at 40° C. for 1 month (40° C.-1M) (IEC)

TABLE 9

Composition of tested formulations

| | Sample No. | | | | | | |
|---|---|---|---|---|---|---|---|
| | 48 | 49 | 50 | 51 | 52 | 53 | 54 |
| Anti-HM1.24 antibody (mg/mL) | 10 | 10 | 10 | 10 | 10 | 10 | 10 |
| Polysorbate 80 (%) | 0.05 | 0.05 | 0.05 | 0.05 | 0.05 | 0.05 | 0.05 |
| Acetate buffer (mM) | 10 | 10 | 10 | 10 | 10 | 10 | 10 |
| Sodium chloride (mM) | 100 | 100 | 100 | 100 | 100 | 100 | 100 |
| PH | 5.50 | 5.75 | 6.00 | 6.25 | 6.50 | 6.75 | 7.00 |

TABLE 10

Evaluation results of heat resistance test (50° C.-1M, 40° C.-1M)

| Sample No. | pH | Residue (%) | GPC (50° C.-1M) Aggregation products (%) | Decomposition product 1 (%) | Decomposition product 2 (%) | IEC (40° C.-1M) Main peak (%) |
|---|---|---|---|---|---|---|
| 48 | 5.50 | 79.1 | 14.5 | 5.4 | 2.5 | 67.2 |
| 49 | 5.75 | 84.2 | 11.3 | 5.8 | 2.3 | 64.4 |
| 50 | 6.00 | 85.6 | 10.0 | 5.9 | 2.2 | 62.5 |
| 51 | 6.25 | 85.5 | 10.1 | 6.1 | 2.2 | 58.5 |
| 52 | 6.50 | 86.8 | 8.6 | 6.5 | 2.2 | 57.8 |
| 53 | 6.75 | 87.1 | 7.9 | 6.8 | 2.2 | 57.0 |
| 54 | 7.00 | 86.5 | 7.7 | 7.6 | 2.5 | 55.0 |

On the basis of these results, it is confirmed that, in the range of pH 5.5 to pH 6.5, the formation of aggregation products and the transition into charged heteromolecules were suppressed. Further, the following were confirmed.

The formation of aggregation products was accelerated under lower pH conditions.

The formation of decomposition product 2 was not substantially dependent on pH.

The formation of decomposition product 1 was accelerated at higher pH.

The residue level of the main peak in IEC was higher at lower pH.

Example 4

Dependency on Sodium Chloride Concentration

The heat resistance test was conducted to study the effect of sodium chloride concentration on the stability of the anti-HM1.24 antibody.

(1) Test on 2.5 mg/mL Formulations

The evaluation was conducted as follows. Tables 11 and 12 show the composition of tested formulations and the results obtained, respectively.
Test sample: 1 mL per 5 mL vial (Samples 55-58)
Evaluation: heat resistance test
Storage conditions: at 50° C. for 3 months (50° C.-3M) (GPC)

TABLE 11

Composition of tested formulations

| | Sample No. | | | |
|---|---|---|---|---|
| | 55 | 56 | 57 | 58 |
| Anti-HM1.24 antibody (mg/mL) | 2.5 | 2.5 | 2.5 | 2.5 |
| Polysorbate 80 (%) | 0.025 | 0.025 | 0.025 | 0.025 |
| Acetate buffer (mM) | 20 | 20 | 20 | 20 |
| PH | 6.0 | 6.0 | 6.0 | 6.0 |
| Sodium chloride (mM) | 23 | 100 | 200 | 500 |

TABLE 12

Evaluation results of heat resistance test (50° C.-3M)

| Sample No. | NaCl (mM) | Residue (%) | Aggregation products (%) | Decomposition product 1 (%) | Decomposition product 2 (%) |
|---|---|---|---|---|---|
| 55 | 23 | 75.4 | 17.6 | ND | 7.1 |
| 56 | 100 | 76.8 | 15.5 | ND | 7.6 |
| 57 | 200 | 76.5 | 15.8 | ND | 7.8 |
| 58 | 500 | 68.0 | 14.5 | 8.7 | 8.6 |

When sodium chloride was added to the sample such that the final concentration was 500 mM, a reduced residue level of monomeric molecules was observed, whereas the other samples showed no difference in stability.

(2) Test on 10 mg/mL Formulations

The evaluation was conducted as follows. Tables 13 and 14 show the composition of tested formulations and the results obtained, respectively.

Test sample: 1 mL per 5 mL vial (Samples 59-61)
Evaluation: heat resistance test
Storage conditions: at 50° C. for 1 month (50° C.-1M) (GPC)

TABLE 13

Composition of tested formulations

| | Sample No. | | |
|---|---|---|---|
| | 59 | 60 | 61 |
| Anti-HM1.24 antibody (mg/mL) | 10 | 10 | 10 |
| Polysorbate 80 (%) | 0.05 | 0.05 | 0.05 |
| Acetate buffer (mM) | 10 | 10 | 10 |
| PH | 6.0 | 6.0 | 6.0 |
| Sodium chloride (mM) | 100 | 150 | 200 |

TABLE 14

Evaluation results of heat resistance test (50° C.-1M)

| Sample No. | NaCl (mM) | Residue (%) | Aggregation products (%) | Decomposition product 1 (%) | Decomposition product 2 (%) |
|---|---|---|---|---|---|
| 59 | 100 | 90.6 | 7.0 | 4.5 | 1.9 |
| 60 | 150 | 89.2 | 7.6 | 4.5 | 2.0 |
| 61 | 200 | 88.9 | 7.8 | 4.7 | 2.1 |

Over the tested concentration range of sodium chloride (23 to 200 mM), there was no difference in the stability of the anti-HM1.24 antibody formulations.

Example 5

Dependency on Acetic Acid Concentration

The heat resistance test was conducted to study the effect of acetic acid concentration on the stability of the anti-HM1.24 antibody.

(1) Test on 10 mg/mL Formulations

The evaluation was conducted as follows. Tables 15 and 16 show the composition of tested formulations and the results obtained, respectively.

Test sample: 1 mL per 5 mL vial (Samples 59, 62 and 63)
Evaluation: heat resistance test
Storage conditions: at 50° C. for 1 month (50° C.-1M) (GPC)

TABLE 15

Composition of tested formulations

| | Sample No. | | |
|---|---|---|---|
| | 59 | 62 | 63 |
| Anti-HM1.24 antibody (mg/mL) | 10 | 10 | 10 |
| Polysorbate 80 (%) | 0.05 | 0.05 | 0.05 |
| Acetate buffer (mM) | 10 | 20 | 50 |
| pH | 6.0 | 6.0 | 6.0 |
| Sodium chloride (mM) | 100 | 100 | 100 |

TABLE 16

Evaluation results from heat resistance test (50° C.-1M)

| Sample No. | Acetic acid (mM) | Residue (%) | Aggregation products (%) | Decomposition product 1 (%) | Decomposition product 2 (%) |
|---|---|---|---|---|---|
| 59 | 10 | 90.6 | 7.0 | 4.5 | 1.9 |
| 62 | 20 | 89.7 | 7.9 | 4.8 | 2.1 |
| 63 | 50 | 89.0 | 8.3 | 4.9 | 2.1 |

On the basis of these results, it is confirmed that the anti-HM1.24 antibody formulations were stable over the range of 10 to 50 mM acetic acid.

The invention claimed is:

1. A method for suppressing formation of at least one of visible insoluble matter and insoluble particles caused by Fe ions present in an antibody-containing solution formulation, wherein the Fe ions have been introduced into the formulation during a production process of the formulation, which method comprises adding acetic acid to the solution formulation having pH of 5.5-6.5, to thereby suppress the formation of visible insoluble matter or insoluble particles in the antibody-containing solution, wherein the antibody is the humanized anti-interleukin6 receptor IgG antibody hPM-1 or humanized anti-HM1.24 antigen IgG antibody and wherein sodium chloride is added to the solution.

2. The method according to claim 1, wherein the concentration of acetic acid is in the range of 10-50 mM.

3. The method of claim 1, further comprising adding a surfactant to the solution.

4. The method of claim 3, wherein the surfactant is Polysorbate 80 or 10, or a poloaxmer.

5. The method of claim 3, wherein the concentration of the surfactant is 0.01-10 mg/mL.

6. The method according to claim 1, wherein the formation of visible insoluble matter or insoluble particles in the antibody-containing solution formulation is suppressed during storage of the formulation.

7. The method according to claim 1, wherein the acetic acid acts to suppress the formation of visible insoluble matter in the antibody-containing solution.

8. The method according to claim 1, wherein the antibody has been obtained from antibody-producing CHO cells.

9. The method of claim 1 wherein said antibody is an IgG1 antibody.

* * * * *